US009513201B2

(12) United States Patent
Anderson et al.

(10) Patent No.: US 9,513,201 B2
(45) Date of Patent: Dec. 6, 2016

(54) MEASUREMENT OF FLUID PROPERTIES (71) Applicant: SCHLUMBERGER TECHNOLOGY CORPORATION, Sugar Land, TX (US)

(72) Inventors: Valerie Anderson, Hardwick (GB); Gerald Henry Meeten, Ware (GB)

(73) Assignee: SCHLUMBERGER TECHNOLOGY CORPORATION, Sugar Land (*) Notice: Subject to any disclaimer, the term of this patent is extended or adjusted under 35 U.S.C. 154(b) by 200 days.

(21) Appl. No.: 14/103,668

(22) Filed: Dec. 11, 2013

(65) Prior Publication Data

US 2014/0157876 A1 Jun. 12, 2014

Related U.S. Application Data

(60) Provisional application No. 61/736,260, filed on Dec. 12, 2012.

(51) Int. Cl.
*G01N 11/00* (2006.01)
*G01N 11/10* (2006.01)

(52) U.S. Cl.
CPC ....... *G01N 11/10* (2013.01); *G01N 2011/0033* (2013.01)

(58) Field of Classification Search
CPC ...... G01N 11/16; G01N 11/14; G01N 11/00; G01N 33/2888; G01N 11/10; G01N 2011/0033; H01L 2924/00014
USPC ...................................................... 73/54.02
See application file for complete search history.

(56) References Cited

U.S. PATENT DOCUMENTS 3,803,903 A 4/1974 Lin
5,253,513 A * 10/1993 Van Arsdale .......... G01N 11/16
73/54.02

(Continued)

FOREIGN PATENT DOCUMENTS

WO 2005001441 1/2005
WO 2010012975 2/2010

OTHER PUBLICATIONS

Anderson et al., "Interpretation of T-Bar Tool Measurements for Yield Stress Materials," Applied Rheology, 2012, vol. 22(5): pp. 55370-1-55370-8.

(Continued)

*Primary Examiner* — Eric S McCall
*Assistant Examiner* — Mohammed E Keramet-Amircola (57) ABSTRACT

A system and method for measuring physical properties of non-Newtonian fluids, such as fluids containing dispersed solid particulate material and having a yield stress. A fluid resistance member is moved through the non-Newtonian fluid sufficiently slowly that viscous drag on the member is negligible and fluid resistance is essentially due to the yield stress of the fluid. The torque required to maintain the movement of the member through the fluid is measured, and at least one physical property, other than apparent viscosity of the fluid, is determined by employing a known relationship between the measured torque and the physical property of interest.

20 Claims, 7 Drawing Sheets

(56) References Cited

U.S. PATENT DOCUMENTS

| | | | |
|---|---|---|---|
| 6,240,770 B1* | 6/2001 | Raffer | B01L 7/00 73/54.23 |
| 6,330,826 B1* | 12/2001 | Meeten | G01N 11/14 73/152.62 |
| 6,584,833 B1* | 7/2003 | Jamison | E21B 49/005 73/54.28 |
| 6,931,916 B2* | 8/2005 | Zamora | G01N 15/04 210/711 |
| 7,624,625 B2 | 12/2009 | Jau | |
| 7,992,427 B2 | 8/2011 | Tonmukayakul et al. | |
| 8,794,051 B2* | 8/2014 | Morgan | G01N 11/14 73/54.01 |
| 2005/0141338 A1* | 6/2005 | Jarvinen | B28C 7/026 366/2 |
| 2007/0295055 A1* | 12/2007 | Doe | G01N 11/14 73/1.02 |
| 2008/0060423 A1* | 3/2008 | Jau | G01N 11/14 73/54.31 |
| 2010/0162799 A1* | 7/2010 | Andersson | G01L 3/10 73/54.31 |

OTHER PUBLICATIONS

Anonymous, "API Recommended Practice 13B-2: Recommended Practice for Field Testing of Oil-based Drilling Fluids," American Petroleum Institute, 2005: pp. 1-114.

Anonymous, "ANSI/API Recommended Practice 13B-1: Recommended Practice for Field Testing Water-based Drilling Fluids," American Petroleum Institute, 2009: pp. 1-104.

Barnes, "15.2.2.2: The effect on the dispersed phase" and "15.2.2.3: The effect of medium-to-high concentration of particles," A Handbook of Elementary Rheology, University of Wales, Institute of Non-Newtonian Fluid Mechanics, 2000: pp. 122-124.

Chilingarian et al., "Weighting Materials," Developments in Petroleum Science, vol. 11: drilling and drilling fluids, 1983: pp. 240-242.

Darley et al., "Properties of Drilling Fluids: Density," Composition and Properties of Drilling and Completion Fluids, Fifth Edition, Gulf Publishing Company: Houston, 1988: pp. 6-8.

Geehan et al., "The Cutting Edge in Drilling-Waste Management," Oilfield Review, Winter 2006/2007: pp. 54-67.

Mahaut et al., "Yield stress and elastic modulus of suspensions of noncolloidal particles in yield stress fluids," J. Rheol., Jan./Feb. 2008, vol. 52(1): pp. 287-313.

Tehrani et al., "AADE-04-DF-HO-22: Role of Rheology in Barita Sag in SBM and OBM," AADE Drilling Fluids Conference, Apr. 2004: pp. 1-16.

Underhill et al., "SPE 18963: Model-Based Sticking Risk Assessment for Wireline Formation Testing Tools in the U.S. Gulf Coast," SPE International, 1998: pp. 79-89.

Combined Search and Examination Report of British Application No. GB1321818.5 dated Jun. 6, 2014: pp. 1-7.

* cited by examiner

MEASUREMENT OF FLUID PROPERTIES

CROSS-REFERENCE TO RELATED APPLICATION

This application claims the benefit of U.S. Provisional Patent Application Ser. No. 61/736,260 filed Dec. 12, 2012, which is incorporated herein by reference in its entirety.

BACKGROUND

Embodiments of the present invention relate to measuring physical properties of a fluid containing dispersed solid particulate material and having a yield stress. Merely by way of example, such fluids containing dispersed solid particulate material may comprise drilling muds/drilling fluids, which muds/fluids exhibit sag.

The rheological properties of liquids containing a dispersed solids particulate phase are well-studied. Such materials usually have a yield stress and are non-Newtonian in nature.

However it is difficult to measure the rheological properties by traditional rheometric methods. Furthermore, even if measurements of such materials are made it is usually the apparent viscosity which is measured, i.e., the shear stress divided by the shear rate.

However, for non-Newtonian fluids the apparent viscosity has little rheological importance, and is not useful for deriving other physical properties of the fluid.

Drilling muds, employed to assist in the drilling of oil and gas reservoirs are examples of such non-Newtonian fluids. The drilling muds/fluids, like many other fluids containing dispersed solid particulate material, typically have a yield stress, so that any solid particles do not sediment out of the mud/fluid when the mud/fluid is static. However, even with this property, some sedimentation still occurs in drilling muds/fluids in a process that is termed "sag" or "sagging."

A number of methods have been proposed to measure the sag tendency of drilling muds. All of the methods require the attention of a skilled operator, and all use measurement of the vertical density gradient in the drilling mud/fluid to quantify the sag. Although the methods have been described as applying to drilling muds/fluids, the methods of measuring sag are also applicable to other particulate containing fluids, e.g., fluids for cuttings re-injection ("CRI") or the like.

Hydrocarbons such as oil or gas are extracted from underground reservoirs through a well bored into the rock formation by means of a drill bit connected to a drill string or coil tubing. Rock cuttings are removed from the bit by means of a drilling fluid or mud that is pumped down the pipe or coil tubing. This mud/fluid returns the cuttings generated by the drill bit as it bores through the rock to the surface via the annulus formed between the outside of the drill string and the inner-wall of the wellbore created in the formation. At the surface, cuttings that are larger than about 150 microns are removed from the drilling mud/fluid by shale-shaker screens. In order to maintain wellbore stability, the pressure of the mud/drilling fluid at any depth in the wellbore should exceed the pressure of liquid in the pore space of the formation (known as the "pore pressure") so as to prevent flow of formation fluids into the wellbore.

To provide for maintaining a pressure in the wellbore that exceeds the pore pressure, generally the drilling mud is "densified" by the addition of a finely divided weighting agent, typically barite particles, but often other minerals or a combination of minerals may be used, where the weighting agent density exceeds the un-weighted mud density. The weighting agent is added to the mud in a quantity that is determined to be sufficient to achieve the desired mud density. The lower limit of the particle size of the weighting agent is selected such that it does not affect the mud's rheology or damage the permeability of the formation in a reservoir section. An upper limit of the particle size is given by the mesh size of the shale shaker screens used to remove cuttings from the circulated mud. Merely by way of example, the size may lie in the 10 micron to 100 micron range.

Being of this size, the particles are not suspended by Brownian motion and so are prone to sediment under the influence of gravity; this process is termed "sag." Sag causes variations in the density of the drilling mud, both in the borehole, and as it emerges at the surface. Sag can lead to many problems; e.g., well-control, fracturing of the uncased formation with lost circulation, and the sticking of the drill pipe or other down hole hardware in beds of sagged weighting material.

For drilling muds in a cased or uncased hole the yield stress is a factor in the tendency of wireline logging tools and cables to stick in the hole. Thus the invention proposes a novel means of quantifying sag in general, and also a means that relates specifically to the sticking of wireline hardware.

Additionally, in cuttings re-injection (CRI), rock cuttings from a well are separated from the drilling mud via a shaker screen and ground to a specified maximum size (typically 300 micron) and slurried with seawater and usually a polymer to give a fluid. This fluid is pumped downhole to fracture a rock formation, hence disposing of the cuttings. The slurry viscosity is required to be as small as possible to minimize the friction pressure drop in the pipework and the fracture, but large enough to suspend the cuttings during the transit time from the surface pumps to the fracture. Careful design and sag measurement of CRI fluids is required to avoid unwanted sedimentation of the cuttings.

Thus, a method of testing such fluids to produce useful information as to their physical properties would be desirable.

SUMMARY

In one embodiment of the present invention, a method of measuring physical properties of a non-Newtonian fluid is provided, such as a fluid containing dispersed solid particulate material and having a yield stress. In the embodiment, a fluid resistance member may be moved through the non-Newtonian fluid sufficiently slowly that viscous drag on the member is negligible and fluid resistance is essentially due to the yield stress of the fluid. Torque required to maintain the movement of the member through the non-Newtonian fluid may be measured and at least one physical property of the fluid, other than apparent viscosity, may be determined from a known relationship between the measured torque and the physical property of interest.

In one embodiment of the present invention a system of measuring physical properties of a non-Newtonian fluid is provided. The system may comprise a container for holding the non-Newtonian fluid and a fluid resistance member. A device may be used to move the fluid resistance member or the non-Newtonian fluid such that the fluid resistance member moves through/relative to the non-Newtonian fluid sufficiently slowly that viscous drag on the fluid resistance member is negligible and fluid resistance is essentially due to the yield stress of the fluid. A sensor may be used for measuring a torque of/applied to the fluid resistance member as it moves through the non-Newtonian fluid. In some aspects a processor may be used to process the physical properties of the non-Newtonian fluid from the torque.

BRIEF DESCRIPTION OF THE DRAWINGS

The present disclosure is described in conjunction with the appended figures. It is emphasized that, in accordance with the standard practice in the industry, various features are not drawn to scale. In fact, the dimensions of the various features may be arbitrarily increased or reduced for clarity of discussion.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In a first aspect, embodiments of the present invention relate to a method of measuring physical properties of a non-Newtonian fluid, such as a fluid containing dispersed solid particulate material and having a yield stress, the method comprising moving a fluid resistance member through the fluid sufficiently slowly that viscous drag on the member is negligible and fluid resistance is essentially due to the yield stress of the fluid, measuring the torque required to maintain the movement of the member through the fluid, followed by deriving at least one physical property, other than apparent viscosity of the fluid, by employing a known relationship between the measured torque and the physical property of interest.

A desirable physical property of the fluid to be measured is the volume fraction of solids, v, because this can provide other useful information regarding the fluid.

For example, for viscosity there is the established Kreiger-Dougherty law which describes the enhanced viscosity $\eta(v)$ caused by adding particles to an initially particles-free Newtonian fluid of viscosity $\eta(0)$, to make suspension of volume fraction v. This law teaches that $$\eta(v)=\eta(0)(1-v/v_M)^{-5v_M/2} \qquad (1)$$

where: $v_M$ is the (notional) volume fraction at which $\eta(v)$ becomes infinite.

For the yield stress, Mahaut F, Chateau X, Coussot P, Ovarlez G, YIELD STRESS AND ELASTIC MODULUS OF SUSPENSIONS OF NONCOLLOIDAL PARTICLES IN YIELD STRESS FLUIDS, J. Rheol. 52:287 (2008), describe the enhanced yield stress $\tau_Y(v)$ caused by adding particles to an initially particles-free fluid of yield stress $\tau_Y(0)$ to make suspension of volume fraction v. This law teaches that $$\tau_Y(v) = \tau_Y(0)(1-v)^{1/2}(1-v/v_M)^{-5v_M/4} \quad (2)$$

where: $v_M$ is the (notional) volume fraction at which $v_Y(v)$ becomes infinite.

Equations 1 and 2 may be compared with a law that describes the enhanced density $\rho(v)$ caused by adding particles to an initially particles-free fluid of density $\rho(0)$ to make suspension of volume fraction v. This law teaches that $$\rho(v) = (1-v)\rho(0) + v\rho_P = \rho(0) + v(\rho_P - \rho(0)) \quad (3)$$

where: $\rho_P$ is the material density of the particles.

Equations 1, 2 and 3 may be used to establish that the measurable quantities of rheology and density depend on the volume fraction v of the particles. The solids volume fraction is however difficult to measure, as such the solids volume may be derived from other measurable parameters, e.g., together with relationships like those discussed above.

However, the inventors have found that yield stress is more sensitive than density to the volume fraction of the solid particles. Thus, in embodiments of the present invention, the measurement of yield stress may be used to provide a more accurate measure of solids volume fraction. In embodiments of the present invention, a physical property that is derived from the measured torque is the yield stress of the non-Newtonian fluid.

In the method in accordance with one embodiment of the present invention, the movement of the fluid resistance tool is rotational, as this motion provides the simplest way to have a continuous and constant speed through the fluid.

In embodiments of the present invention, any conveniently-shaped object, such as a sphere or a cylinder, may be used to produce a torque M when rotated in a fluid that possesses a yield stress. Thus for an axially-symmetric object rotated around a vertical symmetry axis z whose radius r(z) depends on z, M is given by $$M = \tau_Y \int_{z=0}^{z=Z} r(z) dA \quad (4)$$

where: dA is an element of the surface area.

Thus for a sphere of radius a, Eq. 4 gives $$M = \frac{8\pi}{3} a^3 \tau_Y, \quad (5)$$

hence showing the principle that the desired quantity $\tau_Y$ is obtained from the measured torque M and the geometry parameter of the tool.

Once the yield stress of the fluid is obtained, in accordance with an embodiments of the present invention, as discussed above, the yield stress may be used to further obtain the volume fraction of the solids in the fluid, e.g., by equation (2). In embodiments of the present invention, the volume fraction of solids may be used to obtain the density of the fluid, also as discussed above, e.g., in equation (3).

As discussed above, another aspect of non-Newtonian fluids/fluids containing particulate/solids is the tendency of the fluids to exhibit sag, which is caused by partial sedimentation of the solid material. This produces a solids volume fraction vertical gradient which changes over time.

Thus, the solids volume fraction is a function of vertical position and it would be desirable to obtain information regarding the gradient.

In such a case, knowledge of the volume fraction of solid as it varies with the depth of the fluid is of interest. Thus, in an embodiment of the present invention, measurements of yield stress may be made as a function of depth of fluid and/or of time.

Although the principle of obtaining yield stress from measured torque is demonstrated above by the spherical tool, it may be extended to other tools. For example, in embodiments of the present invention, when measuring the vertical yield stress gradient, a fluid resistance member with a minimum vertical height may be used to achieve greater resolution. Thus, in some embodiments, the fluid resistance member has a vertical height of less than 10 mm, more or less than 5 mm.

In addition, in embodiments of the present invention, the fluid resistance member may be configured to allow solids particles to pass through it from above, so that it does not interfere with any naturally occurring sedimentation.

In embodiments of the present invention, the fluid resistance member may comprise a straight slender rod of circular section rotated about its short axis by a shaft mid-way and normal to the rod's length. Such a tool when rotated in the horizontal plane has been shown to disturb a fluid over a height similar to a diameter D of the rod, e.g., about 0.5 to 1.5 mm. If the rod length is L the measured torque is given by $$M_Y = \alpha_R D L^2 \tau_Y / 4 \quad (6)$$

where the term $\alpha_R = 10$. Thus, in accordance with an embodiment of the present invention, by measurements of $M_Y$ at various heights in a vessel that contains a material that sediments slowly over the time of measurement, Eq. 6 allows the height-dependence of the yield stress $\tau_Y$ to be obtained as a measure of the dense sagged material in the material.

In embodiments of the present invention, the fluid resistance member to measure yield stress is moved slowly, for example of the order of 0.001 to 0.01 $s^{-1}$ (for a rotation of the order of 0.01 to 0.1 rpm) in order to be sensitive predominantly to the fluid's rheology rather than its density. Slow rotation may also be used to make the tool most sensitive to yield stress rather than viscosity. Additionally, the slow rotation, in accordance with aspects of the present invention, may minimize mixing or homogenization of the fluid.

In order to obtain information regarding the vertical yield stress gradient and thus the solids volume fraction gradient it is necessary to probe the fluid at various heights through the fluid. Thus, in embodiments of the present invention, the movement of the fluid resistance member is provided at a plurality of different heights in the fluid.

Additionally or alternatively the height of the fluid resistance member can be fixed and the changes in yield stress over time can give useful information regarding the sedimentation behaviour of the fluid.

As such fluids have a yield stress, if the fluid is not exposed to shear it is capable of slowing or preventing complete sedimentation of the solids material. However if the fluid is exposed to shear then it is no longer capable of preventing the solids from sedimenting due to its yield stress. Such a situation is termed 'dynamic sag'.

Thus in one embodiment, the method of the present invention is carried out with the fluid under investigation being exposed to induced shear other than that provided by the fluid resistance member.

When measuring dynamic sag, it is not generally necessary to obtain information on the vertical solids volume fraction gradient, however it is generally more interesting to monitor the changes in solids volume fraction at one vertical point over time.

In embodiments of the present invention, the measuring location is provided below the shearing zone and there is a small gap between them. This configuration is used to prevent the fluid resistance member picking up any rheological effects from the sheared zone of the fluid.

Thus in another aspect, the present invention relates to an apparatus for measuring the dynamic sag of a fluid comprising dispersed solid particulate material and having a yield stress, the apparatus comprising a chamber comprising a region wherein the fluid subjected to a controlled shear environment, and positioned beneath the shearing region, a fluid resistance member capable of moving through the fluid to measure the torque required to maintain said movement.

Typically the fluid resistance member is as described above for use in the method.

In embodiments of the present invention, the chamber is cylindrical and the controlled shear region is provided by a cylindrical wall coaxially located within the cylindrical chamber. This configuration creates an annular region, within which the fluid is sheared in a controlled manner.

Thus, in an embodiment of the present invention, in use the solid particles sediment through the fluid in the sheared region and the fluid resistance member measures the increase in torque required to maintain a constant movement speed through the fluid positioned below the sheared region.

As discussed above, the use of yield stress $\tau_Y$ as a measure of sag has an advantage over other parameters as the yield stress, may, in aspects of the present invention, be measured with minimal intrusion as is described below. For example, the yield stress of the weighting agents barite (density 4200 kg m$^{-3}$) and calcium carbonate (density 2700 kg m$^{-3}$) may be measured in accordance with an embodiment of the present invention.

Figure 1:
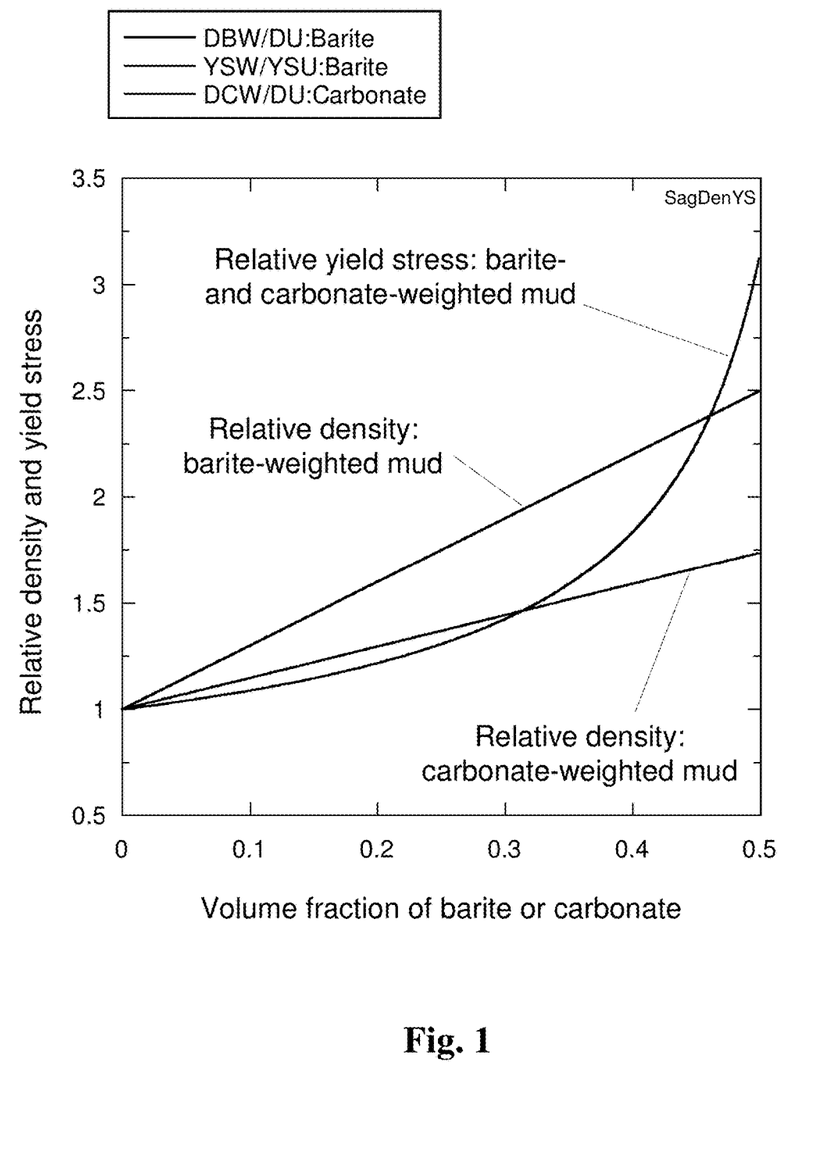
FIG. 1 is a graph plotting relative density and relative yield stress for a volume fraction of barite.

FIG. 1 plots the relative density $\rho(v)/\rho(0)$, and the relative yield stress $\tau_Y(v)/\tau_Y(0)$, calculated using Eqs. 3 and 2, respectively, where $v_M$ was taken as 0.55. The yield stress is shown to be sensitively dependent on the volume fraction $v$ of the weighting agent, and has the same functional form for both barite and calcium carbonate, and indeed for all types of agent. In contrast, the relative density of the barite-weighted and the carbonate-weighted fluids depends on the density of the weighting agent.

Thus, measuring the yield stress in accordance with aspects of the present invention provides, among other things, a more accurate measure of volume fraction of solids than measuring density.

Figure 2:
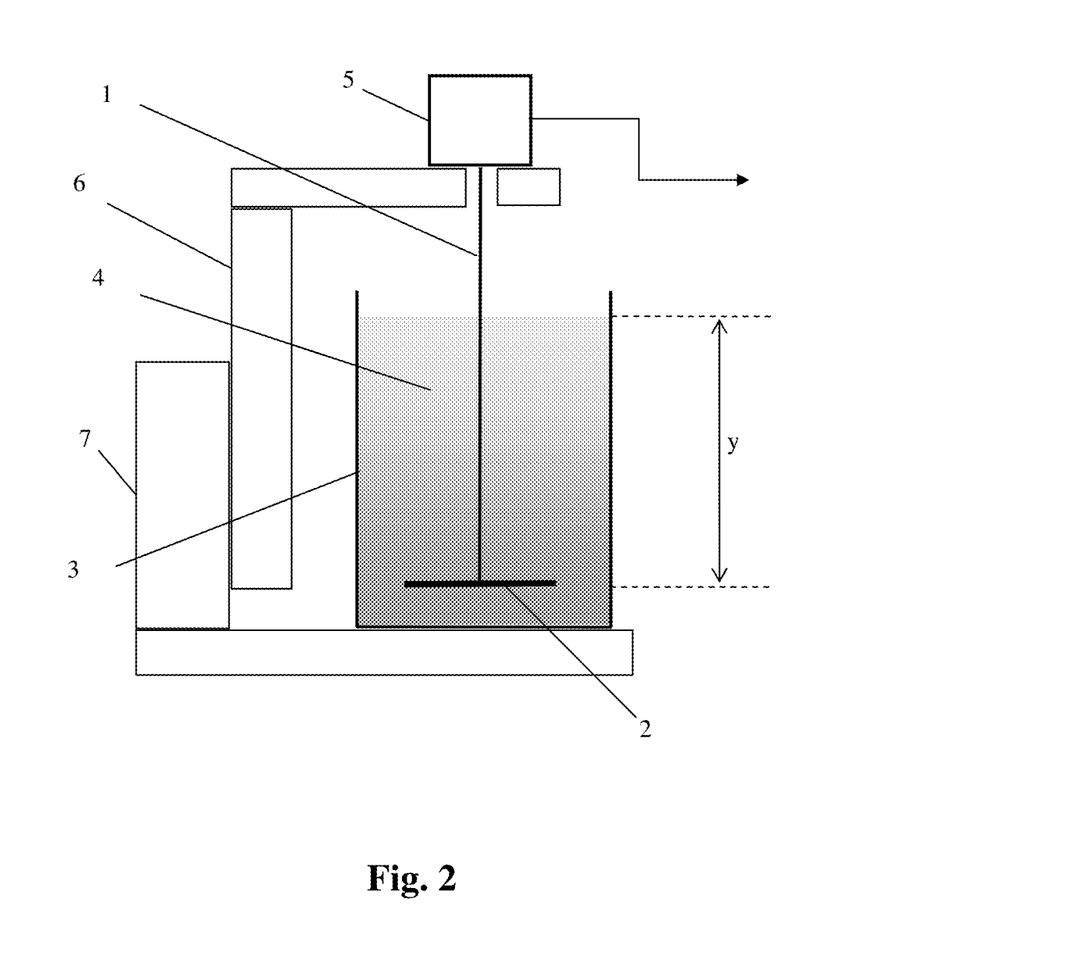
FIG. 2 illustrates a system for determining fluid resistance comprising a member, i.e., a T-bar tool, in accordance with an embodiment of the present invention.
Figure 3:
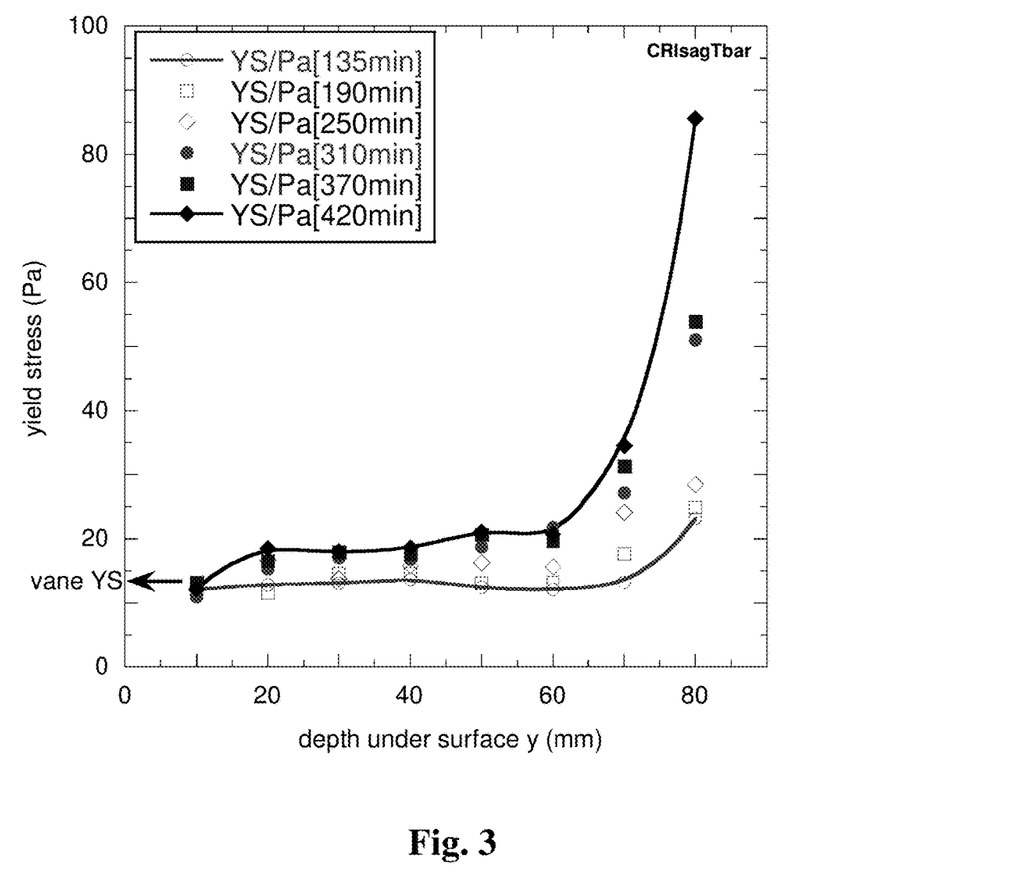
FIG. 3 illustrates torque M increases with depth y, and time, in a manner that characterizes the sagging process.

FIG. 2 shows a fluid resistance member, i.e., the T-bar tool, in accordance with an embodiment of the present invention, comprising a shaft 1, that may be rotated slowly, a thin bar 2, that may be disposed in some aspects close to the bottom of a vessel 3, which vessel 3 contains a sagging fluid 4 (non-Newtonian fluid). In embodiments of the present invention, the T-bar tool may be rotated at a steady angular speed ω by a drive unit 5, which may drive the shaft at a slow angular speed ω, and may also, in some aspects, be used to measure the torque M applied to the shaft resulting from the yield stress of the fluid. The drive and torque-measuring unit 5 is attached to a rigid piece 6 that can slide vertically along a piece 7, and via a mechanism (not shown) which allows the T-bar to access different heights in the sagging fluid, as measured by y. As the dense particles accumulate towards the base of the vessel 3 the torque M increases with depth y, and time, in a manner that characterizes the sagging process, e.g., as shown for a cuttings re-injection fluid in FIG. 3.

An alternative mode of use is to keep the T-bar close to the base of the vessel and to measure the torque as time increases. Applicants have found that the hydrodynamic interaction of the T-bar with a nearby solid boundary is negligible for a yield stress fluid, if the boundary is distant by more than a few T-bar diameters.

Figure 4:
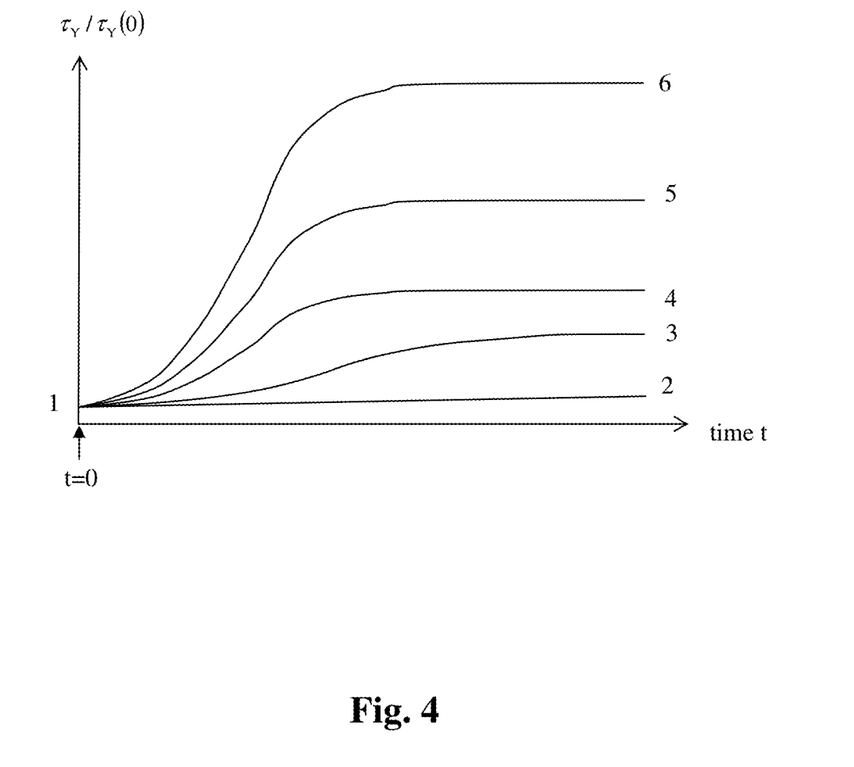
FIG. 4 shows schematically time-dependence of relative yield stress $\tau_y(t)/\tau_y(0)$ for various fluids, where $\tau_y(t)$ is the yield stress at a time t, and $\tau_y(0)$ is the yield stress at time t=0.

FIG. 4 shows schematically the time-dependence of the relative yield stress $\tau_Y(t)/\tau_Y(0)$ for various fluids, where $\tau_Y(t)$ is the yield stress at a time t, and $\tau_Y(0)$ is the yield stress at time t=0. Equation 6 shows that $\tau_Y(t)/\tau_Y(0)=M_Y(t)/M_Y(0)$. Thus FIG. 4 shows $\tau_Y(t)/\tau_Y(0)=1$ at t=0, as expected. Curve 2 shows a fluid for which the sag is small, while curves 3, 4, 5, and 6 show a sag of increasing severity as measured by the magnitude of $\tau_Y(t)/\tau_Y(0)$ after a long time. Similarly, the curves 3, 4, 5 and 6 show that the time over which sag occurs is accessible from the measurement. Thus for some engineering applications a small short-time sag may be acceptable, even though the long-time sag is severe.

Figure 5:
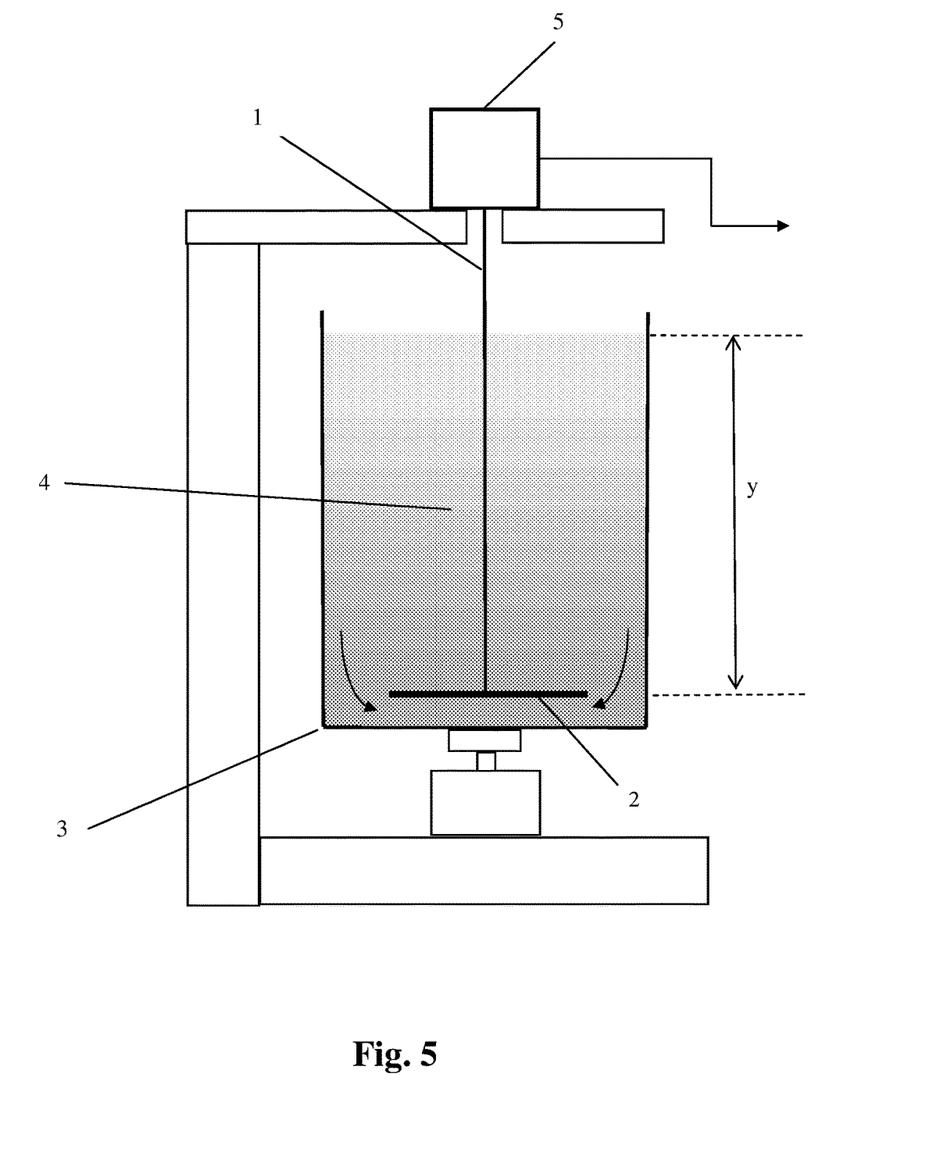
FIG. 5 illustrates a system for measuring fluid properties using a torque sensor, in accordance with an embodiment of the present invention.

FIG. 5 shows an alternative embodiment of the method described previously (FIG. 2), where the T-bar 1 and 2 and the vessel and fluid 3 and 4 are as previously, but 5 is a torque sensor, and does not rotate the T-bar, as previously. In embodiments of the present invention, the relative motion between the T-bar and the fluid is given by a motor 6 attached to and rotating the vessel 3. The essential physical principles are identical to the method described previously (FIG. 2), and the embodiment of FIG. 5 could also be used in the mode where the T-bar depth y below the fluid surface is varied as shown in FIG. 2. The separation of torque measurement and the rotation in the embodiment of FIG. 5 has advantages (to be described) for the measurement of dynamic sag.

As previously described, dynamic sag occurs when the fluid is sheared. Thus the following examples now described combine the T-bar measurement of sag via rheology, particularly yield stress, with an externally-imposed shear.

Figure 6:
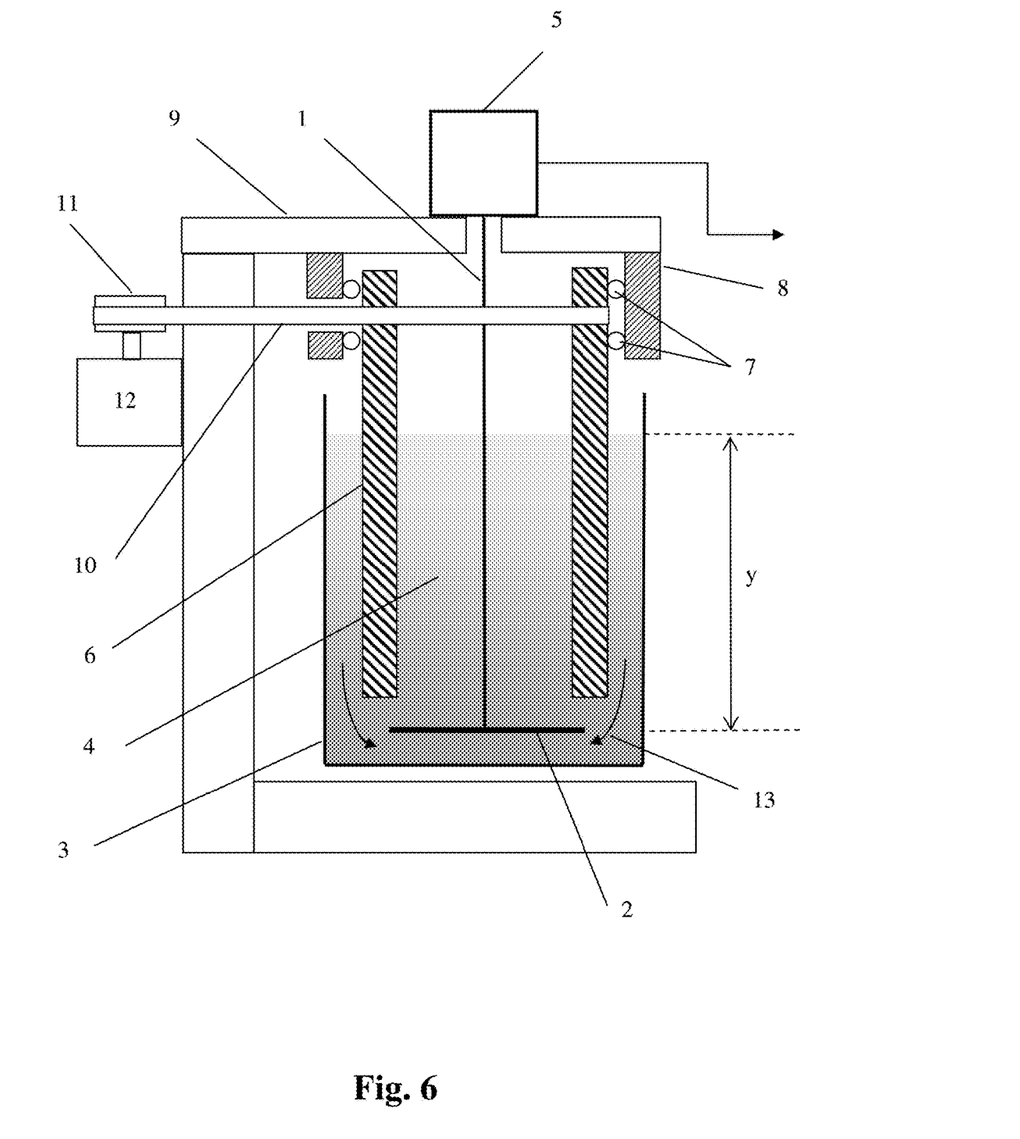
FIG. 6 shows a system for measuring fluid properties in which a shaft rotates a T-bar located near an internal base of a vessel for holding a fluid to be tested, in accordance with an embodiment of the present invention.

FIG. 6 shows an embodiment in which the shaft 1 rotates a T-bar 2 located near the internal base of the vessel 3 which holds the fluid 4, similar to the static sag embodiments previously described herein. Thus 5 is a combined torque sensor and rotor, which rotates the T-bar at a steady angular speed ω, and also measures the torque M required to maintain that speed.

The shear required to produce dynamic sag occurs in the annular gap between the inside diameter of the vessel 3, and the outside diameter of the hollow cylinder 6. In embodiments of the present invention, bearings 7 connect the hollow cylinder 6 to a cylindrical support 8 fixed to an upper frame member 9, and allow the hollow cylinder 6 to rotate around an axis coincident with the axis of the shaft 1. In embodiments of the present invention, such rotation at a chosen angular speed ω is enabled by means of a belt 10, driven by a pulley 11 of a motor 12.

Dynamic sag is caused by shear of the fluid in the gap between the outer radius of hollow cylinder 6, and the inner radius of vessel 3. In practice dynamic sag depends on the shear rate D, which in the embodiment shown in FIG. 6 is given approximately by:

$$D = \frac{\omega(a+b)}{2(b-a)},\quad(7)$$

where: a is the outer radius of the cylinder 6, and b is the inner radius of the vessel 3.

The dense particles undergoing sag sediment down the gap, as shown by arrows 13, and form a bed of enhanced concentration and yield stress, which, in embodiments of the present invention, is sensed by the T-bar 2. In this embodiment the vertical distance between the T-bar 2 and the lowest part of the hollow cylinder 6 may, in some aspects of the present invention, be at least several T-bar diameters, to avoid torque from the cylinder 6 being transmitted to the T-bar.

Figure 7:
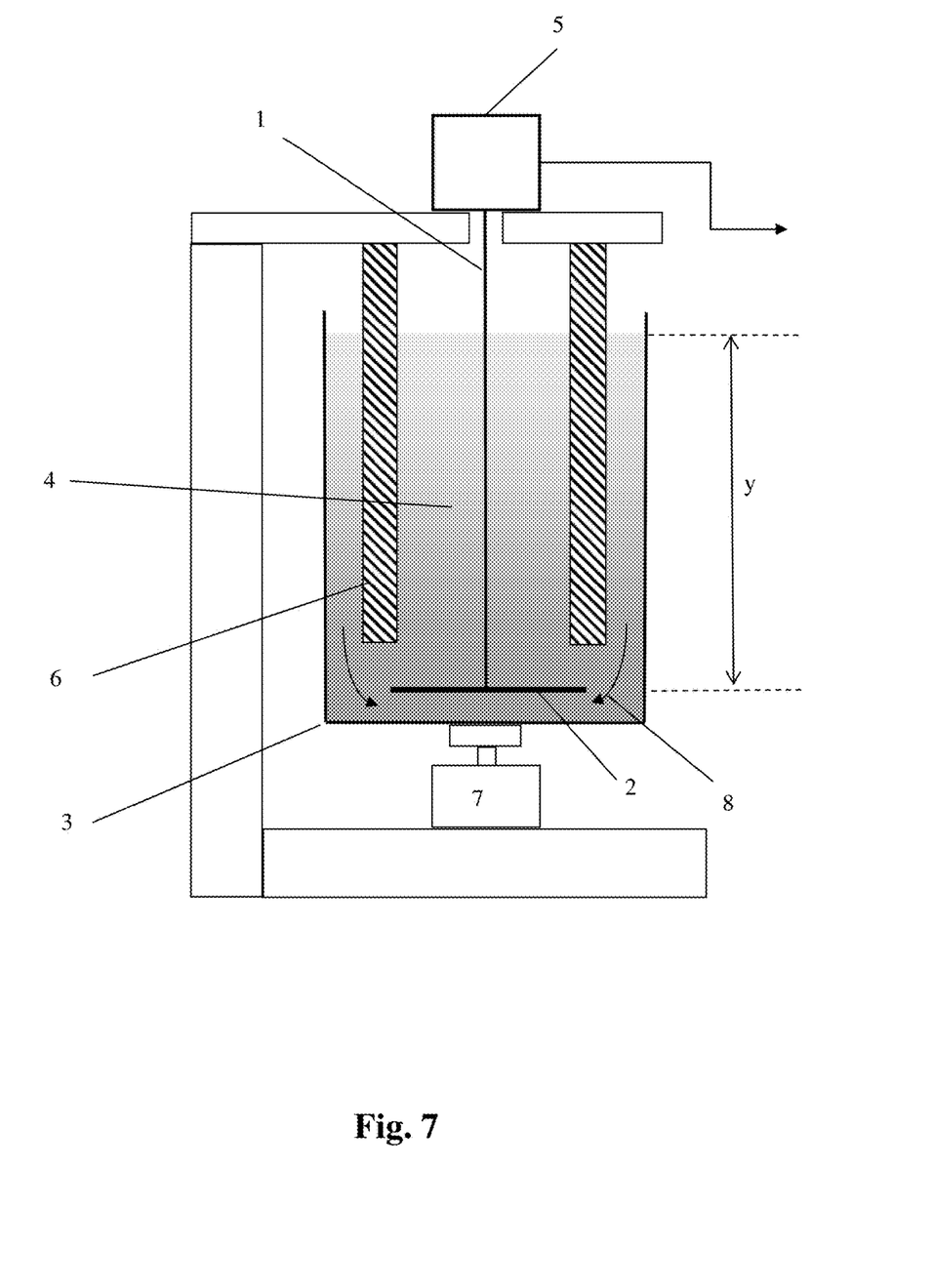
FIG. 7 illustrates a system for measuring fluid properties in which a shaft 1 connects a T-bar to a torque sensor for measuring torque acting on the T-bar, in accordance with an embodiment of the present invention.

FIG. 7 shows an embodiment in which the shaft 1 connects the T-bar 2—located near the internal base of the vessel 3, which holds the fluid 4—to a torque sensor 5 which measures the torque M acting on the T-bar. Rotation of vessel 3 by means of motor 7 produces the shear required to produce dynamic sag in the annular gap between the inside diameter of the vessel 3 and the outside diameter of the hollow cylinder 6.

The amount of dynamic sag depends on the shear rate D, which in the embodiment shown in FIG. 7 is given approximately by Eq. 7; where a is the outer radius of the cylinder 6, and b is the inner radius of the vessel 3. The dense particles undergoing sag sediment down the gap as shown by arrows 8 and form a bed of enhanced concentration and yield stress on the internal base of vessel 3. The sedimentary bed is rotated by vessel 3, and the torque arising from the yield stress is sensed by T-bar 2.

In this embodiment the rotation of the vessel 3 has two separate functions: (i) to shear the fluid in the gap between the outer radius of hollow cylinder 6 and the inner radius of vessel 3, in order to initiate dynamic sag; and (ii) to rotate the sediment relative to the T-bar in order to measure the torque arising from the yield stress.

The angular speeds for functions (i) and (ii) may be incompatible, e.g., 100 rpm to produce a practical amount of barite sag and 0.1 rpm to measure the torque between the T-bar and the sediment. In embodiments of the present invention, this may be overcome by alternation of the angular speed with time e.g., an angular speed of 100 rpm for 5 min to obtain dynamic sag, followed by an angular speed of 0.1 rpm for 1 min to obtain the yield stress torque.

While the principles of the disclosure have been described above in connection with specific apparatuses and methods, it is to be clearly understood that this description is made only by way of example and not as limitation on the scope of the invention.

What is claimed is:

1. A method of measuring physical properties of a fluid containing dispersed solid particulate material and having a yield stress, the method comprising:
    holding a quantity of the fluid within a chamber;
    allowing solid particulate material in the fluid to undergo downward sedimentation while the fluid remains in the chamber;
    moving a fluid resistance member through the fluid at a plurality of different heights within the vessel or at a plurality of different times, with the movement being sufficiently slow that viscous drag on the member is negligible and fluid resistance is essentially due to the yield stress of the fluid;
    at each of the different heights or different times measuring the torque required to maintain the movement of the member through the fluid; and
    deriving at least one physical property, other than apparent viscosity of the fluid, at each of the different heights or different times by employing a known relationship between the measured torque and the at least one physical property and thereby observing a gradient of the at least one physical property with respect to height or with respect to time.

2. A method according to claim 1, wherein the physical property comprises a yield stress of the fluid.

3. A method according to claim 2, wherein the yield stress is further employed to calculate a solids volume fraction of the fluid in the region of the measurement of yield stress.

4. A method according to claim 2, wherein the yield stress is determined from the measured torque and a geometry parameter of the fluid resistance member.

5. A method according to claim 2, wherein the fluid resistance member comprises a T-bar and the yield stress is determined from a relation between the measured torque and the yield stress given by:

$$M_Y = \alpha_R DL^2 \tau_Y / 4.$$

6. A method according to claim 1, wherein the movement of the fluid resistance member is rotational.

7. A method according to claim 1, wherein the method involves the movement of the fluid resistance member and taking measurements of the at least one physical property at a plurality of different heights in the fluid and thereby observing a gradient of the at least one physical property with respect to height.

8. A method according to claim 1 wherein the fluid resistance member has a vertical height of less than 10 mm.

9. A method according to claim 1, wherein the fluid resistance member is a T-bar.

10. A method according to claim 1, wherein the shear rate of the fluid resistance member through the fluid is less than 0.01 s$^{-1}$.

11. A method according to claim 1 wherein the fluid resistance member has a vertical height of less than 5 mm.

12. A method according to claim 1, wherein the shear rate of the fluid resistance member through the fluid is less than 0.001 s$^{-1}$.

13. An apparatus for measuring physical properties of a fluid containing dispersed solid particulate material and having a yield stress, the apparatus comprising:
    a chamber to hold a quantity of the fluid configured so that solid particulate material in the fluid is able to undergo downward sedimentation within the vessel;
    a fluid resistance member extending into the chamber;
    a driver configured to drive the fluid resistance member to rotate through the fluid within the chamber;
    means to vary the vertical position of the fluid resistance member relative to the chamber;
    a sensor for measuring the torque required to maintain the movement of the member through the fluid; and
    a processor configured to process a yield stress of the fluid from the measured torque.

14. The apparatus of claim 13, wherein the fluid resistance member comprises a T-bar.

15. The apparatus of claim 14, wherein the yield stress is processed from the measured torque and a geometry parameter of the fluid resistance member.

16. The apparatus of claim 14, wherein the yield stress is processed from a relation between the measured torque and the yield stress given by:

$$M_Y = \alpha_R DL^2 \tau_Y / 4.$$

17. The apparatus of claim 13, wherein the fluid resistance member comprises a T-bar.

18. An apparatus for measuring the dynamic sag of a fluid comprising dispersed solid particulate material and having a yield stress, the apparatus comprising:

a chamber to hold a quantity of the fluid and comprising a shearing region wherein the fluid is subjected to a controlled shear environment;

a fluid resistance member;

a driver configured to drive the fluid resistance member to move through the fluid; and a sensor to measure the torque required to maintain said movement, wherein the fluid resistance member is positioned beneath the shearing region.

19. An apparatus according to claim 18, wherein the chamber is cylindrical and the controlled shear region is provided by a cylindrical wall coaxially located within the cylindrical chamber.

20. A method of measuring dynamic sag of a fluid containing dispersed solid particulate material and having a yield stress, the method comprising:

holding a quantity of the fluid within a chamber;

subjecting the fluid in a region of the container to controlled shear moving a fluid resistance member through the fluid at a position below the said region, and measuring the torque required to maintain the movement of the member through the fluid.

\* \* \* \* \*